United States Patent [19]

Azam et al.

[11] 4,034,222
[45] July 5, 1977

[54] SYSTEM FOR MEASURING RADIATION DOSES IN RADIOTHERAPY APPARATUS

[75] Inventors: Guy Azam; Rene Boux, both of Paris, France

[73] Assignee: C.G.R.-Mev., Paris, France

[22] Filed: Apr. 12, 1976

[21] Appl. No.: 675,903

[30] Foreign Application Priority Data

Apr. 16, 1975 France .................... 75.11759

[52] U.S. Cl. .................... 250/355; 250/336; 250/385
[51] Int. Cl.² .................... G01J 1/42
[58] Field of Search .......... 250/355, 374, 385, 336; 307/219

[56] References Cited

UNITED STATES PATENTS

| | | | |
|---|---|---|---|
| 2,401,289 | 5/1946 | Morgan et al. | 250/355 |
| 3,479,603 | 11/1969 | Overstreet | 307/219 |
| 3,906,233 | 9/1975 | Vogel | 250/355 |
| 3,914,623 | 10/1975 | Clancy | 328/127 |
| 3,959,653 | 5/1976 | Lee | 250/374 |

*Primary Examiner*—Harold A. Dixon
*Attorney, Agent, or Firm*—Karl F. Ross; Herbert Dubno

[57] ABSTRACT

A system for measuring radiation doses in radiotherapy comprises two identical metering networks energized in parallel from a common radiation source, each network including an integrating amplifier whose time constant is variable by the short-circuiting of an input resistor. A manually or automatically reversible switch selectively foreshortens the time constant of one or the other amplifier whereby the corresponding metering network controls the cutoff of the radiation source whenever the emitted radiant energy reaches a predetermined value. The other network, acting as a backup, takes over the radiation cutoff upon failure of the controlling network; this takeover may be indicated by a set of signal lamps jointly controlled by the reversing switch and by a counting unit of the standby network.

6 Claims, 2 Drawing Figures

SYSTEM FOR MEASURING RADIATION DOSES IN RADIOTHERAPY APPARATUS

This invention relates to a circuitry for measuring and controlling the irradiation dose supplied by a radiotherapy apparatus. This system comprises two parallel measuring chains which are associated with a safety system for automatically switching off the radiation source when a predetermined irradiation dose has been reached. In practice, only one chain is normally in operation, the second chain being an auxiliary chain which measures the irradiation dose with a slight delay in relation to the first chain and which is designed to trigger an automatic cutoff of the radiation source in the event of defective operation of the first chain. Such a system, however, can function with a defective auxiliary measuring chain without detection of this fault, which creates a safety hazard.

The object of our present invention is to obviate this disadvantage.

A system according to our invention, designed to measure and control the amount of radiant energy emitted by a radiation source, comprises a pair of substantially identical metering networks or chains energized by radiation-sensing means in the path of a radiant beam originating at the source to be controlled, these networks generating and accumulating respective electrical parameters —such as a succession of pulses —proportional to the sensed radiation. The accumulation of the generated parameter in either network can be selectively retarded with the aid of adjustable delay means, namely an impedance in an integrating circuit, under the control of switchover means operable to assign to one network the role of the controller and to the other network the role of backup, with either manual or automatic interchange of these roles from time to time. The network with the temporarily faster accumulation, i.e. the controller, normally reaches a predetermined limit for the generated parameter —i.e. a certain count for its pulses —earlier than the other network, i.e. the backup, thereby deactivating the radiation source with the aid of disabling means connected to both networks. In the event of a malfunction of the controlling network, however, the backup network takes over the disablement of the radiation source after a short delay.

According to another feature of our invention, the system includes indicator means such as a set of lamps for signaling the existence of a malfunction, i.e. the fact that the deactivation of the radiation source has been initiated by the network which has been assigned the role of backup, the indicator means being therefore jointly controlled by the switchover means and by the two networks. The above and other features of our invention will now be described in detail with reference to the accompanying drawing in which.

Figure 1:
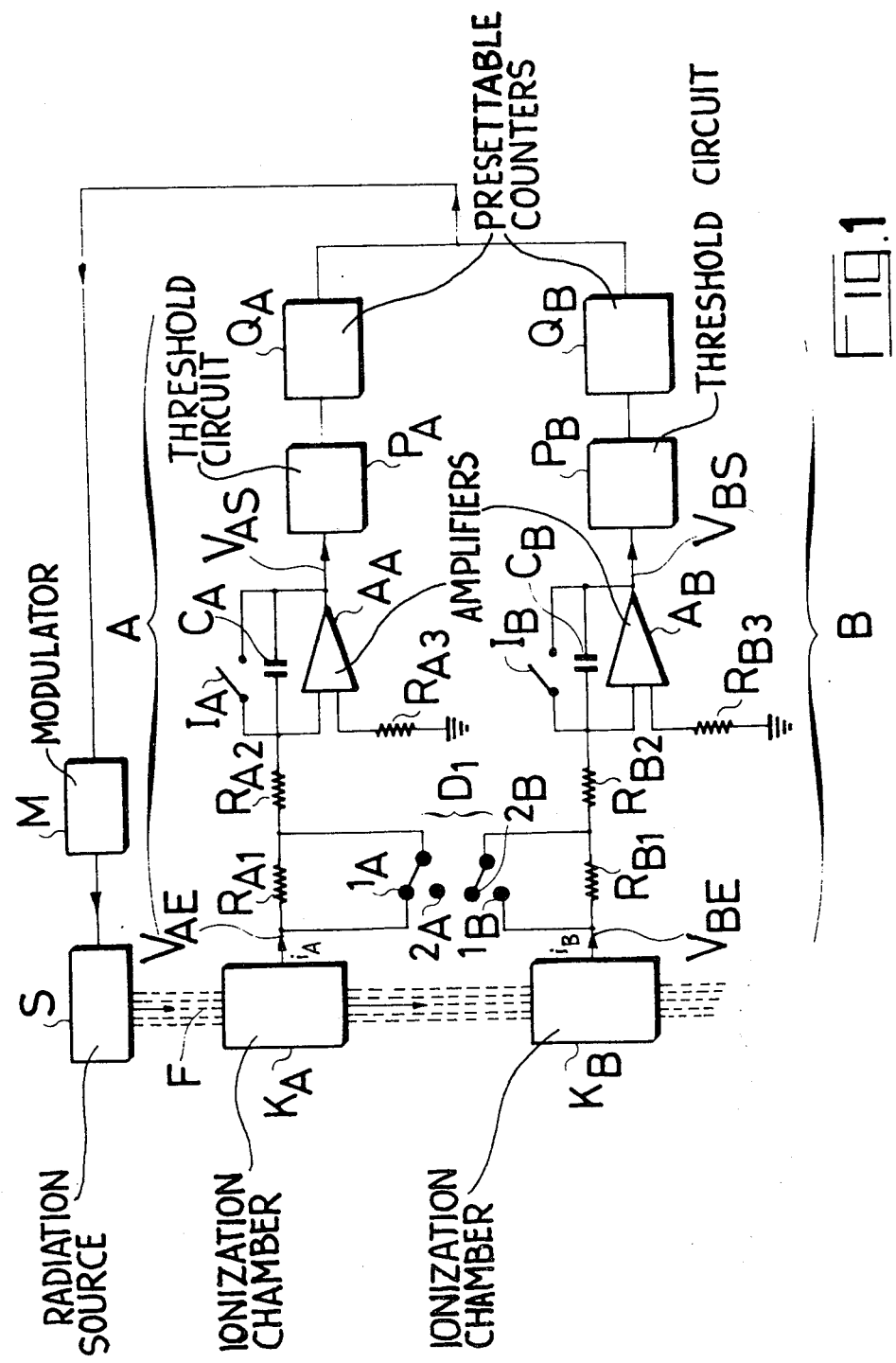
FIG. 1 shows a system according to the invention.

As shown in FIG. 1, a system for measuring and controlling an irradiation dose according to the invention comprises two metering networks or chains A and B designed to control cutout of a radiation source S when the irradiation dose reaches a predetermined level.

Chain A comprises:

(1A) a radiation sensor here consisting of an ionization chamber $K_A$ arranged in the path of a radiation beam F, this ionization chamber $K_A$ being provided with electrodes (not shown) which collect a current $i_A$ to which corresponds a voltage $V_{AE}$ proportional to the intensity of the radiation beam; and (2A). a voltage-frequency converter including
two series resistors $R_{A1}$ and $R_{A2}$ feeding the voltage VAE to an input of
an operational amplifier $A_A$ which delivers a signal $V_{AS}$ proportional to the voltage $V_{AE}$, another input of this amplifier being grounded through a resistor $R_{A3}$,
a threshold circuit $P_A$ driven by amplifier $A_A$,
a presettable counter $Q_A$ stepped by circuit $P_A$ for accumulating a parameter; proportional to the radiant energy detected by sensor $K_A$, and
a capacitor $C_A$ connected across the amplifier $A_A$, this capacitor $C_A$ being dischargeable by the temporary closure of a circuit breaker $I_A$ controlled by the threshold circuit $P_A$.

The second chain B comprises the same elements as the chain A, namely:

(1B). an ionization chamber $K_B$ (in fact the two ionization chambers $K_A$ and $K_B$ may be replaced by a single ionization chamber provided with several electrodes) collecting a current $i_B$ to which corresponds a voltage $V_{BE}$ proportional to the intensity of the radiation beam; and (2B) a voltage-frequency converter including:
two series resistors $R_{B1}$ and $R_{B2}$ feeding the voltage $V_{BE}$ to an input of --;
an operational amplifier $A_B$ which delivers a signal $V_{BS}$ proportional to the voltage $V_{BE}$, another input of this amplifier being grounded through a resistor $R_{B3}$,
a threshold circuit $P_B$, driven by amplifier $A_B$,
a presettable counter $Q_B$ stepped by circuit $P_B$ for accumulating a parameter (pulse count) proportional to the energy picked up by sensor $K_B$, and --;
a capacitor $C_B$ connected across the amplifier $A_B$, this capacitor $C_B$ being dischargeable by the temporary closure of a circuit breaker $I_B$ controlled by the threshold circuit $P_B$.

In operation, when the output voltage $V_{AS}$ (or $V_{BS}$) of the integrating amplifier $A_A$ (or $A_B$) reaches a predetermined value (threshold level), the threshold circuit $P_A$ (or $P_B$) emits a pulse which advances the counter $Q_A$ (or $Q_B$) by one digit and causes the circuit breaker $I_A$ (or $I_B$) to close for a period of time which, although fairly brief, is long enough to enable the capacitor $C_A$ (or $C_B$) to discharge. Thus, the value registered by the counter $Q_A$ (or $Q_B$) corresponds to the integrated amount of radiation, or dose.

A reversing switch $D_1$ 1A, 1B and 2A, 2B controls the insertion or networks of the resistors $R_{A1}$ and $R_{B1}$ in the measuring chains insertion or networks A and B, respectively. In Fig. 1, the resistor $R_{A1}$ is short-circuited while the resistor $R_{B1}$ is effective, introducing a certain delay into the measurement of the dose level by chain B in relation to measurement of the dose level by chain A which thus becomes the principal chain intended to control the automatic cutout of the source of radiation when the dose reaches a predetermined value. In the event of defective operation of the principal chain (chain A in the illustrated position of switchover means $D_1$), the secondary or auxiliary chain B, which charges its shunt capacity slightly more slowly than chain A, triggers the automatic cutout of the radiation source. Depending upon the position of the switch $D_1$, either chain A or chain B functions as the principal chain, or controller the other chain becoming the secondary chain or backup. The switch $D_1$ may be reversed from time to time either manually or better still by an automatic system comprising a preset counter or integrator responsive to the duration, the dose or the number of treatments. A modulator M, receiving a cutoff signal from whichever counter $Q_A$ or $Q_B$ first reaches its preset counting limit, turns off the source S (which may be an accelerator of charged particles) when the desired quantity of radiation has been emitted. With switch $D_1$ engaging its contacts $1_A$ and $1_B$ as shown, metering network or chain A has a higher proportionality factor between its pulse rate and the radiation intensity detected in ionizaton chamber $K_A$ so that the shunt capacitor $C_A$ of its integrating operational amplifier $A_A$ charges faster than the capacitor $C_B$ of amplifier $A_B$ to the level established by the associated threshold circuit whereby counter $Q_A$ is stepped more rapidly than counter $Q_B$. If network A functions normally, therefore, modulator M is triggered by counter $Q_A$ to disable the radiation source; with the resulting disappearance of beam F, no further pulses are generated in either network so that counter $Q_B$ is stopped short of its preset count. If, however, a malfunction in network A prevents the counter $Q_A$ from sending out the cutoff signal, counter $Q_B$ continues to advance to the point where its output triggers the modulator M to terminate the radiation emission.

Figure 2:
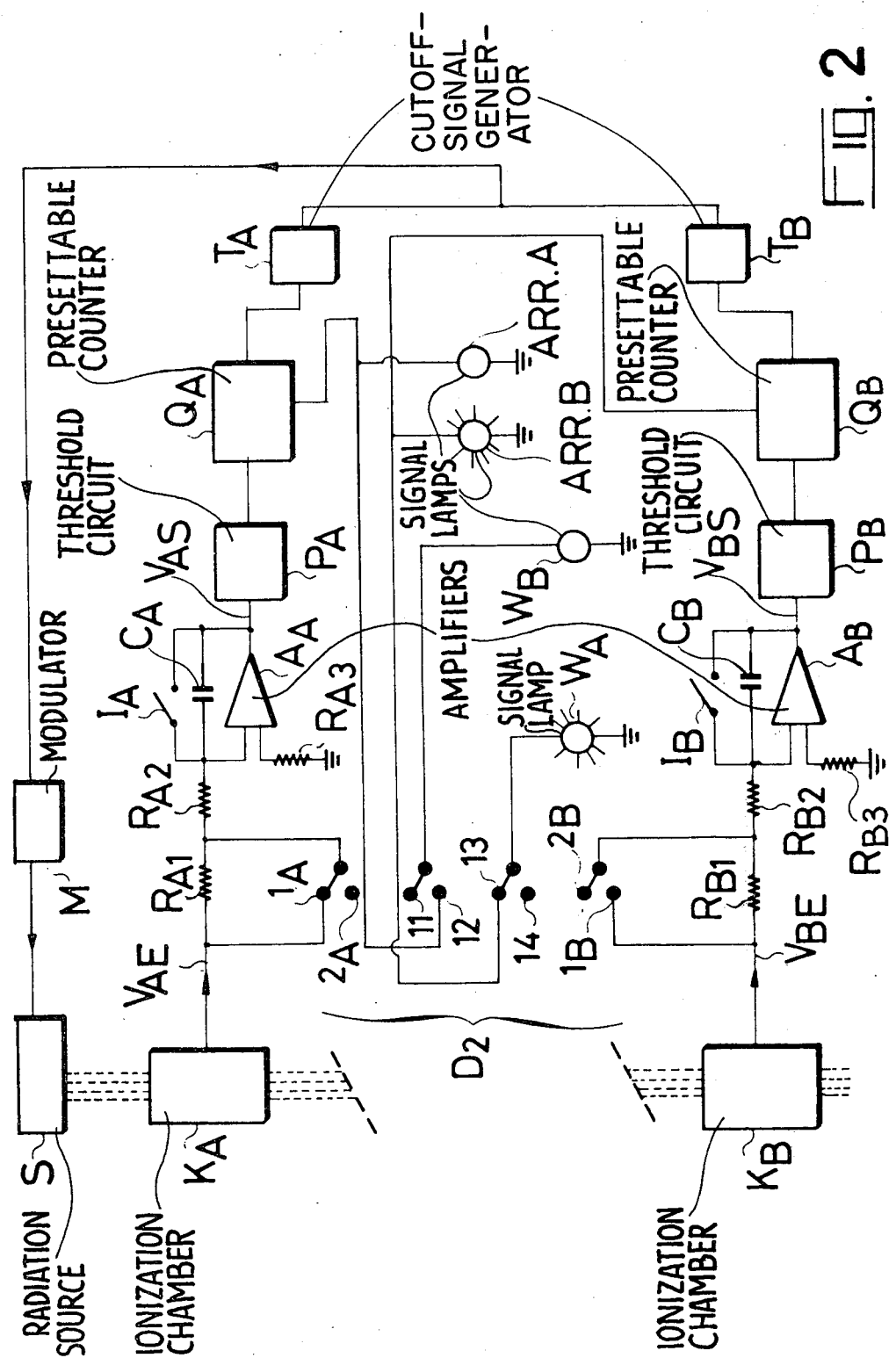
FIG. 2 shows a modification of the embodiment illustrated in FIG. 1.

In FIG. 2 we have shown a modification of the circuitry of FIG. 1 wherein the two-armature switch $D_1$ has been replaced by a four-armature switch $D_2$ having additional contacts 11–14. Counters $Q_A$ and $Q_B$ are here shown connected to modulator M not directly but via respective cutoff-signal generators $T_A$ and $T_B$. This system also includes indicator means in the form of four signal lamps $W_A$, $W_B$, ARR.B and ARR.A, the former identifying one of the two chains as the controlling network while the latter serve to reveal a takeover of control by the respective backup network. In the illustrated position of switch $D_2$, with resistor $R_{A1}$ again short-circuited by contact $1_A$, network A is the controller as indicated by the lighting of signal lamp $W_A$ from an output of counter $Q_B$ by way of contact 13, in parallel with lamp ARR.B. With switch contact 12 open-circuited, an analogous energizing circuit from an output of counter $Q_A$ to lamp $W_B$ is broken; lamp ARR.A, connected to the same output, is is extinguished as soon as this counter reaches the preset limit and trips the cutoff-signal generator $T_A$. With normal operation, therefore, lamp ARR.B stays on and lamp ARR.A goes off at the end of an operating cycle in which lamp $W_A$ is lit; in the opposite switch position, lamp $W_B$ lights in lieu of lamp $W_A$ and lamp ARR.B is extinguished at the end of a cycle in the absence of a malfunction. Thus, a fault in network A (or B) is indicated by the simultaneous lighting of lamps $W_A$ and ARR.A (or $W_B$ and ARR.B) with lamp ARR.B (or ARR.A) turned off.

These signaling lamps could be replaced by logical circuitry in a computer programmed to register a malfunction upon coincidence of the illustrated switch position with a cutoff signal from generator $T_B$ (fault in network A) or upon coincidence of the opposite switch position with a cutoff signal from generator $T_A$ (fault in network B). The malfunction indication may be read out in clear text, signaled by pilot lamps or displayed on a screen.

What we claim is:

1. A system for measuring and controlling the amount of radiant energy emitted by a radiation source comprising:

radiation-sensing means in the path of a radiant beam originating at the radiation source to be controlled;

a pair of substantially identical metering networks connected to said radiation-sensing means for generating and accumulating respective electrical parameters proportional to the sensed radiation;

adjustable delay means in each of said networks for selectively retarding the accumulation of the generated electrical parameter in either of said networks whereby one of said networks operates as a controller normally reaching a predetermined limit for the accumulated electrical parameter earlier than the other of said networks;

disabling means connected to said networks for deactivating said source upon attainment of said predetermined limit by either of said networks, said other of said networks serving as a backup taking over the control of said disabling means in the event of a malfunction of said one of said networks; and switchover means coupled with said adjustable delay means for selectively interchanging the roles of said networks as a controller and as a backup.

2. A system as defined in claim 1 wherein each of said networks includes an integrating circuit with a capacitor for the accumulation of a charge proportional to the sensed radiation, threshold means connected to said integrating circuit for discharging said capacitor upon said capacitor upon said charge reaching a predetermined level, and counting means stepped by said threshold means, said disabling means being responsive to registration of a predetermined count by said counting means, said delay means including an impedance in said integrating circuit.

3. A system as defined in claim 2 wherein said impedance comprises a resistor in series with said capacitor, said switchover means including contacts for alternately short-circuiting said resistor in either one of said networks.

4. A system as defined in claim 2 wherein said integrating circuit comprises an operational amplifier shunted by said capacitor.

5. A system as defined in claim 2, further comprising indicator means jointly controlled by said switchover means and by said counting means for signaling the deactivation of said source by said other of said networks in the event of a malfunction of said one of said networks.

6. A system as defined in claim 5 wherein said indicator means comprises first and second signaling means responsive to said counting means of the backup network for respectively identifying the network selected as the controller and revealing the takeover of the control by the backup.

\* \* \* \* \*